United States Patent [19]

Weissman

[11] Patent Number: 4,781,585
[45] Date of Patent: Nov. 1, 1988

[54] DENTAL ROUTER

[75] Inventor: Bernard Weissman, New York, N.Y.

[73] Assignee: Ipco Corporation, White Plains, N.Y.

[21] Appl. No.: 14,719

[22] Filed: Feb. 13, 1987

[51] Int. Cl.⁴ .............................................. A61C 3/06
[52] U.S. Cl. ..................................................... 433/51
[58] Field of Search ........................ 433/49, 50, 51, 52

[56] References Cited

U.S. PATENT DOCUMENTS

| 0,158,932 | 1/1875 | Gilbert | 433/127 |
| 1,617,523 | 2/1927 | Irish | 433/51 |
| 2,414,056 | 1/1947 | Nieman | 433/51 |

FOREIGN PATENT DOCUMENTS 3108674 9/1982 Fed. Rep. of Germany ........ 433/51

Primary Examiner—Gene Mancene
Assistant Examiner—Adriene J. Lepiane
Attorney, Agent, or Firm—Helfgott & Karas

[57] ABSTRACT

A router for performing finishing operations on a dental model having a housing with a base in which a motor is positioned. A storage compartment mounted on the base includes a pivotal cover. The cover forms a horizontal work platform on which the dental model is supported during the operations. The motor extends into the storage compartment and a tool is secured to the shaft for vertical projection above the work platform through a hole in the cover. Apertures in the cover permit dust to fall down into the storage compartment from which a vacuum extracts the dust. A novel method of routing dental models is provided wherein the dental model is placed on a horizontal work surface and finished using a vertically oriented tool.

20 Claims, 3 Drawing Sheets

DENTAL ROUTER

BACKGROUND OF THE INVENTION

This invention relates to dental apparatus, and more particularly to a router for performing finishing operations onto a dental model.

In preparing dental models, appropriate dies and working casts are made in order to prepare an appropriate dental model. Once completed, portions of the dental model must be properly finished. For example, the lingual portion may be cut out, interfering or objectionable undercuts are removed and portions are smoothed out. Additionally, after the dental model is cut into sections using a saw, each of the sections are trimmed in order to permit non-interfering and matching interface for repositioning of the sections of the dental model. Additional finishing operations also include indexing of the model sections to create undercuts appropriate for repositioning.

Typically, a rotating device such as a router or drill head is utilized for such finishing operations. The dental model is held in one hand and the router is held in the other hand or mounted and placed on a work surface. The router is typically positioned horizontally and the dental model and router are moved against each other, or the hand held model moves against the router.

One of the difficulties in holding the model by hand and moving it against a horizontal shaft is that the model can easily break. Such breakage can occur either through dropping, or excessive hand-pressure, or hitting the model. Furthermore, in working with a held model against a horizontal rotating shaft, it is not possible to get predictable and repeatable results. Since it is a hand operation, each cut and trim is unique. This, therefore, makes it very awkward to provide repeatable undercuts for indexing sections of the model for proper replacement. It also prevents proper mating interlocking sections since it is not possible to predict the exact cut, depth or shape. In fact, certain type of cuts, such as a way, have been difficult, if not impossible to achieve using such prior art arrangements.

SUMMARY OF THE INVENTION

Accordingly, it is an object of the present invention to provide a dental router which avoids the problems of prior art devices.

Another object of the present invention is to provide a dental router having a vertically oriented rotating shaft.

A further object of the present invention is to provide a router for performing finishing operations on a dental model having a horizontal work platform with a rotating operating tool projecting upwardly from the working platform.

Still a further object of the present invention is to provide a router for performing finishing operations on a dental model where the dental model can be retained on a working platform and moved against a vertically projecting rotating operating tool whereby the finishing operations can be appropriately controlled.

Another object of the present invention is to provide a router for performing finishing operations on a dental model which permits safe use of the operating tool and avoids the possibilities of breaking the dental model.

Still a further object of the present invention is to provide a router for performing finishing operations on a dental model which permits quick connection of the operating tools and easy replacement of tools as needed.

Briefly, in accordance with the present invention, there is provided a router for performing finishing operations on a dental model. The router includes a housing having a base portion with a motor positioned in the base portion. A rotating drive shaft extends from a motor. Mounted onto the base portion is a storage compartment with a pivotal cover member closing onto the compartment. A hole is provided in the cover member aligned with the drive shaft and a plurality of apertures are also formed in the cover around the hole. The exterior top surface of the cover member forms a horizontal work platform on which the dental model can be supported during finishing operations. The upper end of the drive shaft serves as a chuck portion and extends into the storage compartment. An operating tool can be secured into the chuck portion for vertical projection above working platform through the hole in the cover. During operation, dust resulting from the finishing operations can fall into the storage compartment through the peripheral apertures. A vacuum outlet from the storage compartment is utilized for extraction of the dust.

The tools are screwed into the chuck in a rotational direction opposite to the rotation of the drive shaft. The cover member has a safety switch so that when lifted, the drive motor is disconnected. Other features are also provided to make this into a safe and easy to utilize apparatus.

There is also described a method of finishing off the surface of a dental model including the steps of supporting the dental model on a horizontal work platform and moving the dental model against a vertically oriented, rotating operating tool which projects upwardly through the work platform. Various types of tools can be inserted in order to achieve numerous types of finishing operations.

Because of the method and apparatus, the type of finish or cut can be accurately controlled for reproducible results. Also, proper undercuts can be generated with mating interfaces in order to reposition the sections of the dental model in place.

The aforementioned objects, features and advantages of the invention will, in part, be pointed out with particularity, and will, in part, become obvious from the following more detailed description of the invention, taken in conjunction with the accompanying drawing, which forms an integral part thereof.

BRIEF DESCRIPTION OF THE DRAWINGS

In the drawings.

In the various figures of the drawing like reference characters designate like parts.

DESCRIPTION OF THE PREFERRED EMBODIMENT

Figure 1:
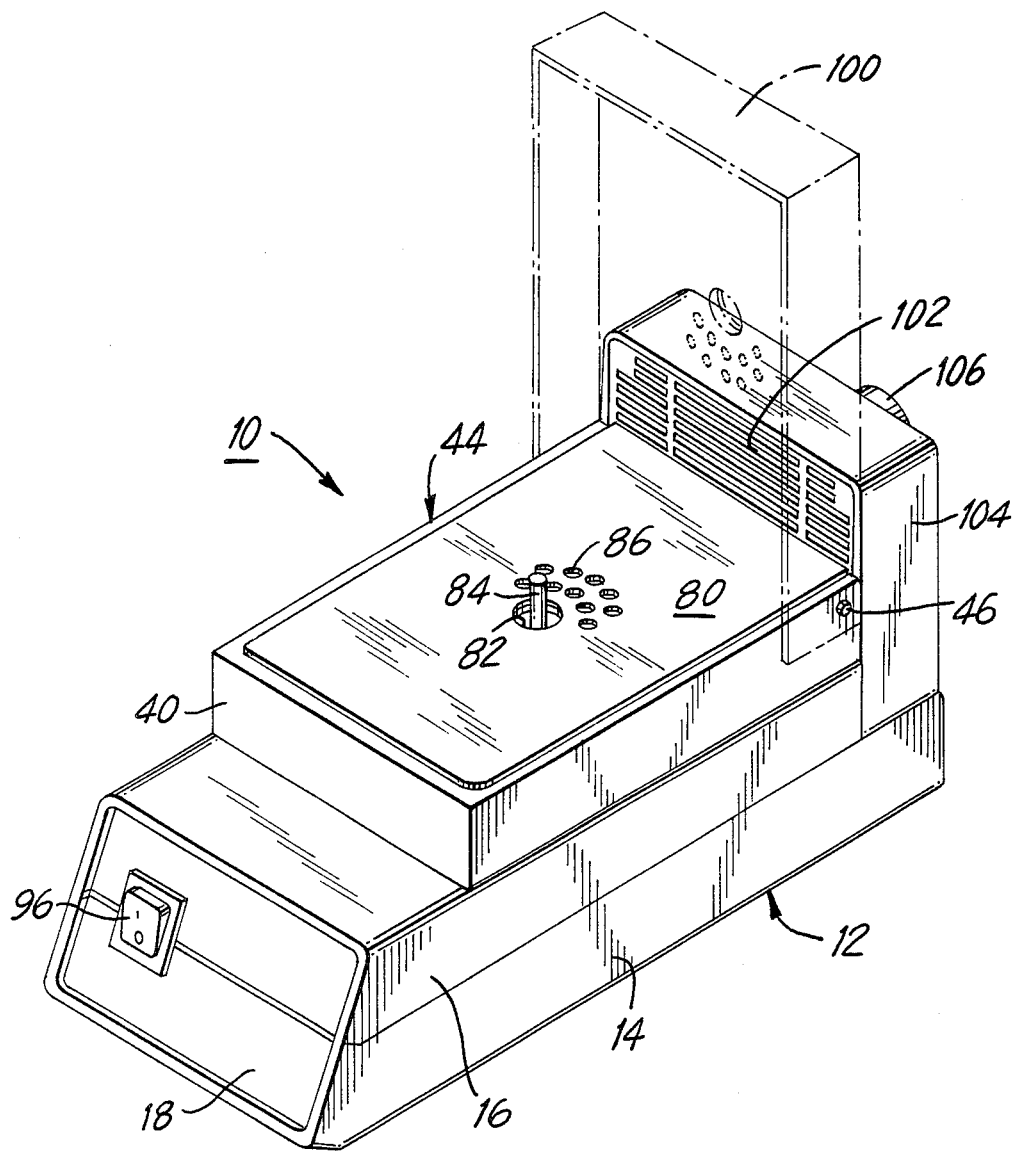
FIG. 1 is a perspective view of the router with the cover member shown in solid lines in its down position and in dotted lines in its raised position.
Figure 2:
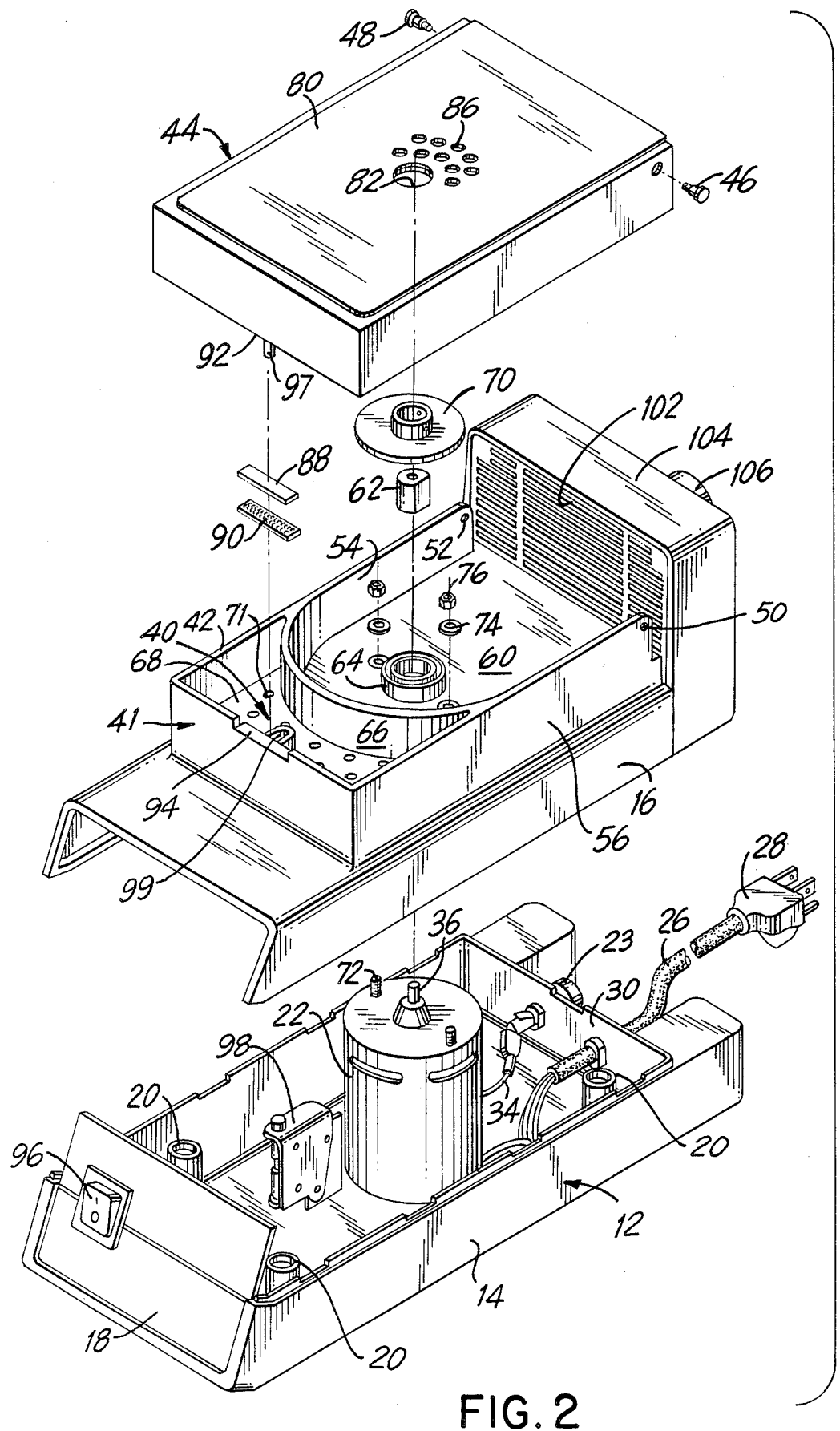
FIG. 2 is an exploded perspective view of the components of the router shown in FIG. 2.

Referring now to FIGS. 1 & 2, the router of the present invention is shown generally at 10 and comprises a base portion 12 formed of a substantially rectangular configuration including a lower pedestal section 14 and an upper section 16 which mate together to form the composite base 12. A front plate spans across the base section. Four receiving posts 20 are provided internally of the pedestal portion 14 for receiving corresponding depending mating posts in the upper portion 16 to secure the two sections together.

Positioned within the composite base portion 12 is a motor 22. A power line 26 with an external plug 28 is connected through the back wall 30 of the pedestal portion for supplying power to energize the motor 22. An external available fuse socket 23 is likewise electrically connected to the circuit through line 34. Upwardly extending from the motor is the drive shaft 36.

Positioned on the base is a raised storage compartment 40 having a substantially horizontal peripheral wall 42. A cover member 44 is pivotally mounted onto the bottom part of the storage compartment. A pair of pivot screws 46, 48 are available for insertion into the threaded apertures 50, 52 in the side walls 54, 56 of the storage compartment for providing the pivotal action.

The peripheral walls of the storage compartment define an interior chamber 60 into which the drive shaft 36 can project. A chuck 62 is mounted onto the drive shaft. A peripheral hub wall 64 surrounds the drive shaft portion projecting upwardly into the chamber 60. An arcuate baffle wall 66 separates the chamber 60 from a front compartment 68 in which tools can be stored in various apertures 71. At the same time, the baffle serves to protect dust from going from the chamber 60 into the forward tool storage compartment 68. Likewise, it protects dust from going into the electronics part of the apparatus.

A slinger member 70 is mounted onto the shaft portion and serves to distribute the dust to a vacuum for removal of the dust, as will hereinafter be described.

The motor is secured in place by means of the threaded studs 72 projecting upwardly into the chamber 60 which are then fastened by means of the washers 74 and the lock nuts 76.

The cover member 44 includes an upper surface 80 which serves as a horizontal working platform. A center bore 82 is aligned with the chuck so that a tool mounted in the chuck projects upwardly in a vertical direction through the bore 82 to be available above the working table 80. A plurality of peripheral apertures 86 are formed about the center bore 82 so that dust accumulating from the routing operation can fall through the working table 80 and fall into the chamber 60.

The cover is secured into its downward position by a pair of opposing interlocking strips 88, 90. One of the strips is mounted on the underside of the front wall of the cover 92. The other strip is mounted in a notched section 94, formed at the front wall of the peripheral wall of the storage compartment.

A main switch 96 is mounted into the front wall 18 for turning on and off of the motor. At the same time, there is provided an interlock switch 97 engaging within a mating portion of the switch in slot 99 such that lifting of the cover, as shown in phantom 100 in FIG. 1, terminates operation of the motor.

At the rear of the apparatus is provided a grillwork 102 which forms the entry into a vacuum chamber 104. An outlet nozzle 106 is provided at the rear of the chamber for interconnection to an external vacuum. Alternatively the vacuum could be formed integrally with the apparatus and directly placed in the chamber 104.

Although the grill work 102 is shown as extending above the level of the working platform 80, it will be appreciated that the upper portion can be solid and the grillwork only provided at the section beneath the platform and specifically at the rear part of the storage compartment.

Figure 3:
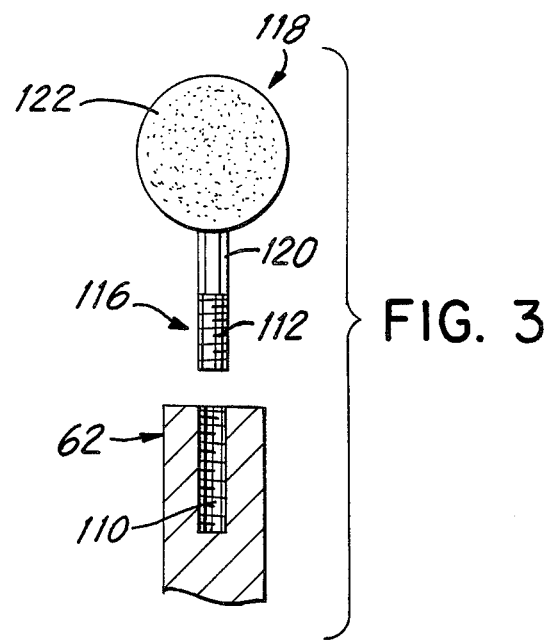
FIG. 3 is an exploded elevational view showing a tool for insertion into the chuck.

As shown in FIG. 3, the chuck 62 includes an internally threaded hole 110 into which is inserted the lower threaded end 112 of the shaft 116 of the tool 118. Above the threaded portion 112 can be provided a section with a flat 120 to facilitate removal of the tool 118 from the chuck 62. The head 122 of the tool would extend upwardly of the working platform surface.

The threaded bore in the chuck is threaded in an opposite direction to the direction of rotation of the motor shaft in order to prevent the tool from loosening during rotation of the motor.

In operation, after the dental working model has been completed, the apparatus of the present invention would be utilized to provide the finishing of the model by shaping it and removing various sections. By way of example, the router would provide smooth cutting and fine finishing of the models in a variety of applications. It can be utilized to remove lingual sections and interfering undercuts on models, as well as creating indices for repositioning articulated models and to make retentive undercuts to hold models firmly in place. The dental model would be placed on the horizontal working surface 80 and held in a horizontal position. The vertical oriented tool projecting above the working surface would then be used by bringing the dental model in contact with the router and moving the dental model around the tool to appropriately shape the model as desired.

It should be appreciated, that the apparatus of the present invention results in a unique method of routing dental models which has heretofore not been utilized. In prior art, there is typically provided a horizontal oriented router and the model would be held directly in the hands without retaining it on a surface. By providing a working table on which the model is oriented, and using a horizontal working table with a vertically oriented tool, accurate and predictable results can be obtained. Furthermore, since only a portion of the tool is exposed, a built in safety mechanism is provided whereby the entire tool is not exposed during operation.

Additional features presented by the apparatus include the quick mounting and dismounting of the tools. Specifically, the cover is pivotally raised from the storage compartment, the tool is removed either by hand or using a manipulating device, such as a wrench, and the tool is rotated out of the chuck. Another tool stored in the storage compartment can be inserted.

Figure 4A:
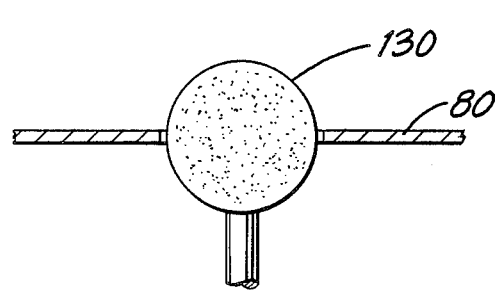
FIGS. 4a, 4b, and 4c, show schematically various tools positioned above the work platform for use in shaping of the dental model.
Figure 4B:
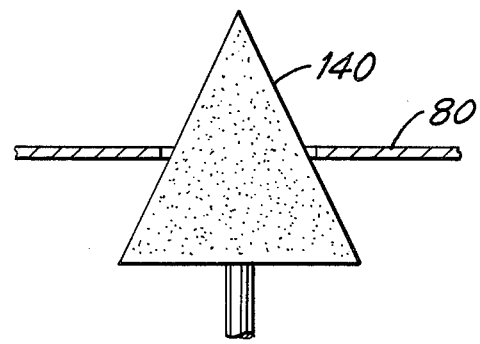
Figure 4C:
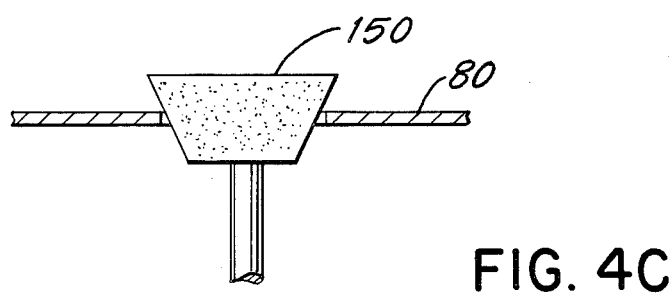

As shown in FIGS. 4a-4c, various tools can be utilized. In FIG. 4a, the tool 130 projecting above the work surface 80 is substantially spherical. However, less than 180 degrees of the tool projects above the surface. In this way, cuts that are made into the dental model would be less than 180 degrees and therefore can be used to provide appropriate means to create non-interfering and matching interfaces for repositioning of models. The spherical cutter can be used for indexing models.

The conical tool shown in FIG. 4b, as 140, projects above the surface 80 and can be used for angle shaping of the side edges of the dental model. It can also be used for creating undercuts to hold models firmly in place when needed.

The tool 150 shown in FIG. 4c and projecting above the table surface 80 can be used for cutting a way in the dental model so that it can be locked in place and repositioned as desired.

There has been described heretofore the best embodiments of the invention presently disclosed. However, changes and modifications may be made thereto without departing from the spirit of the invention.

I claim:

1. A router for performing finishing operations on a dental model, comprising: a housing having a base portion, a motor with a rotating vertical drive shaft secured in said base portion, a storage compartment mounted onto said base portion, a pivotal cover member closing onto said compartment having a hole aligned with said drive shaft, the exterior top surface of said cover member forming a horizontal work platform on which the dental model can be supported during finishing operations, a chuck portion extending from the motor shaft and projecting into said storage compartment and in which an operating tool is secured for vertical projection above the work platform through said hole in said cover for rotation about a vertical axis, a plurality of apertures in said platform peripheral to said hole through which dust resulting from finishing operations can fall into the storage compartment, and a vacuum outlet from said storage compartment through which the dust can be extracted.

2. A router as in claim 1, and further comprising an interlock switch coupled between said cover member and said storage compartment whereby lifting of said cover member stops the motor.

3. A router as in claim 1, and comprising a baffle wall in said storage compartment isolating the dust from entry into the electrical portions.

4. A router as in claim 1, and comprising a slinger plate mounted onto the shaft for directing the dust toward the vacuum outlet.

5. A router as in claim 1, wherein said chuck has an internally threaded bore for receiving a threaded shaft of an operating tool mounted therein.

6. A router as in claim 5, wherein the thread in said bore is such as to cause the operating tool to thread into the chuck in opposite direction to the rotation of the motor shaft.

7. A router as in claim 1, and further comprising a tool storage section in said storage compartments.

8. A router as in claim 7, and further comprising a baffle wall separating said tool storage section from dust.

9. A router as in claim 1, and further comprising an operating tool having a coupling post, external threads on a distal end of said post for threadedly engaging an internally threaded bore in said chuck.

10. A router as in claim 9, and comprising a flat face along a mid portion of said post for engagement with a mounting device for connecting and releasing the operating tool from the chuck.

11. A router as in claim 9, wherein the operating tool is a spherical cutter.

12. A router as in claim 11, wherein the height of said post is such that less than half of the cutter projects above the work platform.

13. A router as in claim 9, wherein the operating tool has a conical shape for angled shaping of the dental model.

14. A router as in claim 9, wherein the operating tool forms a way cut in the dental model.

15. A router as in claim 1, and comprising an air chamber section adjacent said storage compartment, passages from said storage compartment to said chamber section, and an outlet in said air chamber section coupling to a vacuum.

16. A method of finishing the surface of a dental model on a dental router apparatus, comprising: supporting the dental model on a horizontal work platform, and moving the dental model against a vertically oriented, operating tool projecting upwards through the work platform and rotating about a vertical axis.

17. A method as in claim 16 wherein the operating tool is a router and comprising the step of eliminating lingual sections and undercuts.

18. A method as in claim 16, wherein the operating tool is an inverted cone and comprising the step of creating a sequence of uniform, substantially identical undercuts on the dental model.

19. A method as in claim 16, wherein the operating tool is a spherical cutter and comprising the step of forming indexing cuts into the model.

20. A method as in claim 16, and comprising the step of creating non-interfering and matching interfaces on the dental model for repositioning of the model.

* * * * *